(12) United States Patent
Shaw

(10) Patent No.: US 7,160,908 B2
(45) Date of Patent: Jan. 9, 2007

(54) DYNAMIC ANTICANCER PLATINUM COMPOUNDS

(75) Inventor: Jiajiu Shaw, Ann Arbor, MI (US)

(73) Assignee: Unitech Pharmaceuticals, Inc., Ann Arbor, MI (US)

(*) Notice: Subject to any disclaimer, the term of this patent is extended or adjusted under 35 U.S.C. 154(b) by 357 days.

(21) Appl. No.: 10/794,035

(22) Filed: Mar. 4, 2004

(65) Prior Publication Data

US 2004/0176343 A1   Sep. 9, 2004

Related U.S. Application Data

(60) Provisional application No. 60/451,895, filed on Mar. 4, 2003.

(51) Int. Cl.
*A61K 31/41*     (2006.01)
*C07D 231/00*    (2006.01)

(52) U.S. Cl. ............... 514/359; 514/492; 514/184; 548/105; 556/136

(58) Field of Classification Search ........... 548/105; 556/136; 514/359, 492, 184
See application file for complete search history.

(56) References Cited

U.S. PATENT DOCUMENTS

| | | | |
|---|---|---|---|
| 4,140,707 | A | 2/1979 | Cleare et al. |
| 4,207,416 | A | 6/1980 | Hoeschele |
| 4,228,090 | A | 10/1980 | Hydes et al. |
| 4,760,157 | A | 7/1988 | Child et al. |
| 4,797,393 | A | 1/1989 | Farrell et al. |
| 4,808,730 | A | 2/1989 | Bitha et al. |
| 4,937,358 | A | 6/1990 | Bitha et al. |
| 4,996,337 | A | 2/1991 | Bitha et al. |
| 5,107,007 | A | 4/1992 | Farrell |
| 5,178,876 | A | 1/1993 | Khokhar et al. |
| 5,466,678 | A | 11/1995 | Kawabata et al. |
| 5,529,775 | A | 6/1996 | Mikulski et al. |
| 5,844,001 | A | 12/1998 | McClay et al. |
| 5,922,689 | A | 7/1999 | Shaw |
| 5,958,892 | A | 9/1999 | Mukhopadhyay et al. |
| 6,001,817 | A | 12/1999 | Shaw |
| 6,056,973 | A | 5/2000 | Allen et al. |
| 6,130,245 | A | 10/2000 | Shaw |
| 6,297,245 | B1 | 10/2001 | Shaw |
| 6,534,096 | B1 | 3/2003 | Shaw |
| 6,548,541 | B1 | 4/2003 | Shaw |

FOREIGN PATENT DOCUMENTS

| JP | 9-59288 | 3/1997 |
|---|---|---|
| WO | WO 88/02261 | 4/1988 |

OTHER PUBLICATIONS

Colombo et al., 1987, CAS: 106:12460.*
Pasini et al., 1986, CAS: 104:60959.*
Krylova et al., 2000, CAS: 134:47548.*

Berkow, R; Fletcher, A. J., Eds. *The Merck Manual of Diagnosis and Therapy*, 16thEdition, 1992, p. 1280.

Erickson, L. E.; McDonald, J. W.; Howie, J. K.; Clow, R. P. "Proton Magnetic Resonance Studies of Amino Acid Complexes of Platinum (II). I. Synthesis, Spectral Interpretation, and Conformational Implications", *Journal of the American Chemical Society*, 1968, vol. 90, pp. 6371-6373.

Fichtinger-Schepman, A. M. J.; van der Veer, J. L.; den Hartog, J. H. J.; Lohman, P. H. M.; Reedijk, J. "Adducts of the Antitumor Drug *cis*-Diamminedichloroplatinum(II) with DNA: Formation, Identification, and Quantitation," *Biochemistry*, 1985, vol. 24, pp. 707-713.

Abstract of: Giandomenica, C.M.; Abrams, M. J.; Murrer, B. A.; Vollano, J. F.; Barnard, C. F. J.; Harrap, K. R.; Goddard, P. M.; Kelland, L. R.; Morgan, S. E. "Synthesis and Reactions of a New Class of Orally Active Platinum (IV) Antitumor Complexes," *Proceedings of the Sixth International Symposium on Platinum and Other Metal Coordination Compounds in Cancer Chemotherapy*, 1991, pp. 93-100.

Gilman, A. G., Ed. *Goodman & Gilman's The Pharmacological Basis of Therapeutics, Eighth Edition*, 1990, pp. 300-301.

Hollis, L. S.; Amundsen, A. R.; Stern E. W. "Chemical and Biological Properties of a New Series of *cis*-Diammineplatinum(II) Antitumor Agents Containing Three Nitrogen Donors: *cis*-[Pt(NH$_3$)$_2$(N-donor)Cl]$^+$," *Journal of Medicinal Chemistry*, 1989, vol. 32, pp. 128-136.

Kuebler, Jr., J. R., Bailar, Jr., J. C. "The Stereoisomerism of Complex Inorganic Compounds. XIV. Studies Upon the Stereochemistry of Saturated Tervalent Nitrogen Compounds", *Journal of the American Chemical Society*, 1952, vol. 74, pp. 3535-3538.

Miller, B.; Wild, S.; Zorbas, H.; Beck, W. "Synthesis and Biological Activity of *cis*-Dichloro Mono-and Bis(Platinum) Complexes with *N*-Alkyl- Ethylenediamine Ligands," *Inorganica Chimica Acta*, 1999, vol. 290, pp. 237-246.

Miller, S. K.; Marzilli, L. G. "Interaction of Platinum Antitumor Agents with Guanine Nucleosides. $^{195}$Pt and $^1$H NMR Spectroscopic Characterization of Compound III," *Inorganic Chemistry*, 1985, vol. 24, pp. 2421-2425.

Abstract of: Mong, S.; Huang, C. H.; Prestayko, A. W.; Crooke, Stanley T. "Effects of Second-Generation Platinum Analogs on Isolated PM-2 DNA and Their Cytotoxicity in Vitro and In Vivo," *Cancer Research*, 1980, vol. 40(9), pp. 3318-3324.

Peresie, H. J.; Kelman, A. D. "Reactions of Platinum(II) Complexes with Guanine Nucleosides and Nucleotides," *Inorganica Chimica Acta*, 1978, vol. 29, pp. L247-L248.

Pinkard, F. W.; Sharratt, E.; Wardlaw, W.; Cox, E. G., "Isomerides of Quadricovalent Palladium and Platinum", *Journal of the Chemical Society*, 1934, pp. 1012-1016.

(Continued)

*Primary Examiner*—Joseph K. McKane
*Assistant Examiner*—Robert Shiao
(74) *Attorney, Agent, or Firm*—Brinks Hofer Gilson & Lione

(57) ABSTRACT

A series of dynamic platinum compounds for cancer treatment are described. The compounds may become active and inactive reversibly.

19 Claims, 3 Drawing Sheets

OTHER PUBLICATIONS

Abstract of: Plotnikov, V.M.; Kazakov, S. A.; Merkulov, V. G. "Immunobiological Activity of Platinum (II) Coordination Compounds Complexed with Immunoglobulin Fragments," *Byulleten Eksperimental noi Biologii i Meditsiny*, 1989, vol. 108(9), pp. 313-315.

Stewart, D. J.; Dulberg, C. S.; Mikhael, N. Z.; Redmond, M. D.; Montpetit, V. A. J.; Goel, R. "Association of Cisplatin Nephrotoxicity with Patent Characteristics and Cisplatin Administration Methods," *Cancer Chemotherapy and Pharmacology*, 1997, vol. 40(4), pp. 293-308 (including EMBASE Abstract).

Taylor D. M.; Tew, K. D.; Jones, J. D., "Effects of *cis*-Dichlorodiammine Platinum (II) on DNA Synthesis in Kidney and Other Tissues of Normal Tumour-Bearing Rats," *European Journal of Cancer*, 1976, vol. 12(4), pp. 249-254.

Abstract of: Vollano, J. F.; Blatter, E. E.; Dabrowiak, J. C. "DNA Breakage By a Perhydrate Complex of cis-Dichloro-cis-diammine-trans-dihydroxyplatinum (IV) (cis,cis, trans-$Pt(IV)C_{12}(NH_3)_2(OH)_2)$," *Journal of the American Chemical Society*, 1984, vol. 106(9), pp. 2732-2733.

Abstract of: Wondrak, E. M.; Loewer, J.; Kurth R. "Inhibition of HIV-1 RNA-dependent DNA Polymerase and Cellular DNA polymerases $\alpha$, $\beta$ and $\gamma$ by Phosphonoformic Acid and Other Drugs," *Journal of Antimicrobial Chemotherapy*, 1988, vol. 21(2), pp. 151-161.

US 6,458,832, 10/2002, Shaw (withdrawn)

* cited by examiner

DYNAMIC ANTICANCER PLATINUM COMPOUNDS

RELATED APPLICATIONS

This application claims the benefit of U.S. Provisional Application No. 60/451,895, filed Mar. 4, 2003, the entire contents of which are incorporated herein by reference, except that in the event of any inconsistent disclosure or definition from the present application, the disclosure or definition herein shall be deemed to prevail.

FIELD OF INVENTION

This invention relates to a series of dynamic platinum compounds, which may be less toxic than currently available platinum drugs, and to methods of treating cancer by said platinum compounds.

BACKGROUND

Cisplatin, cis-diamminedichloroplatinum (commercial name is Platinol®), has been used as a chemotherapeutic agent for about twenty years since the discovery of its anti-tumor activity by B. Rosenberg. The Oct. 23, 1995 issue of *Chemical & Engineering News* reported, "Cisplatin was first synthesized in the 1800s, but its anticancer activity was not discovered until the 1960s . . . In 1979, it was approved by the Food and Drug Administration (FDA) for clinical treatment of testicular and ovarian tumors and cancers of the head and neck". The Physician's Desk Reference states that cisplatin can be used to treat testicular cancer, ovarian cancer, and bladder cancer.

As a first generation platinum drug, Cisplatin is still being widely used because of its efficacy. However, it is far from being a perfect anticancer drug. Carboplatin (Paraplatin®), was approved by the FDA as the second platinum drug. It appears to have a better therapeutic index than Cisplatin and is more widely prescribed than cisplatin. However, Carboplatin still has significant toxicity and can incur drug resistance from repeat treatment. Recent trends in this field indicate that there may be a renewed interest in finding a significantly improved platinum drug. The third platinum drug, oxaliplatin, has been on European market for a couple of years. Its efficacy is lower than the current platinum drug, but it appears to have lower toxicity. Structures of cisplatin, carboplatin, and oxaliplatin are shown below:

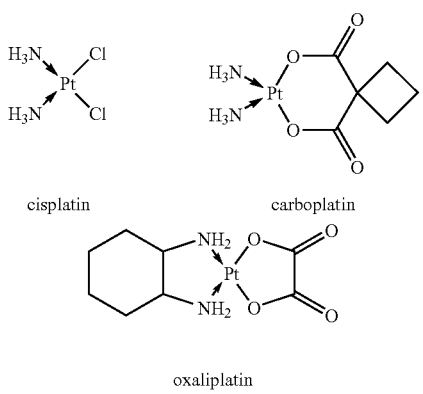

cisplatin    carboplatin oxaliplatin

Problems Associated with Today's Anticancer Platinum Drugs

Cisplatin is known to function as an inhibitor to the DNA replication process; without the ability to replicate, cancer cells eventually die. It is believed that the inhibition is due to the intra-strand cross-linkage between Cisplatin and DNA through the two labile Pt—Cl bonds, especially during the DNA replication process. However, Cisplatin is not very selective in attacking the cells as is carboplatin. As cisplatin and carboplatin destroy cancerous cells, they also damage normal cells.

One of the most critical challenges to improving platinum drugs is to significantly improve the therapeutic index (largely defined as the efficacy/toxicity ratio). An ideal anticancer platinum drug should have a good therapeutic index. Unfortunately, a platinum drug works essentially by killing cancer cells through its cytotoxicity. Thus, increasing the efficacy of such a drug is likely to increase the side effects due to the increased toxicity. This efficacy-toxicity dilemma has hampered the real improvement of platinum drugs for many years.

SUMMARY

The scope of the present invention is defined solely by the appended claims, and is not affected to any degree by the statements within this summary.

In order to significantly improve the performance of platinum drugs, the efficacy-toxicity dilemma must be addressed and solved. Therefore, the objects of this invention include the development of unique platinum compounds that have one or more of the following characteristics as compared with current platinum drugs:

1. The efficacy is substantially maintained.
2. The toxicity is significantly reduced.
3. The platinum compound should be effective for treating certain cancer, including cancers that are not being treated by current platinum drugs.

This invention discloses a series of dynamic platinum compounds that can be used to treat cancer. These dynamic compounds may be divided into two groups herein referred to as "On" and "Off" compounds. Possible mechanisms are shown in FIG. 1 and FIG. 2.

It is well known that the micro-environment of solid tumors is more acidic than the normal biological environment. The difference of the pH values in a cancerous environment and a normal biological environment provides a bio-trigger specifically for the dynamic platinum compounds disclosed in the present invention.

The dynamic platinum compounds designed from the DMP technology allows the platinum compounds to be less active in the microenvironment of normal tissues, which ranges from 7.2 to 7.4, and more active in lower pH environment that usually accompanies solid tumors.

For an "On" compound, such as cis-[Pt(NH$_3$)(NH$_2$—CH$_2$CH$_3$—CO—H)]Cl$_2$, to become active, simple hydrolysis of both Pt—Cl bonds into Pt←OH$_2$ bonds will be sufficient to transform it into an active form similar to that from cisplatin. However, this active form is uniquely differently from that of cisplatin. This active form (1) can chelate with DNA and inhibit the replication of cancer cells, or (2) can be converted to a non-active form under a higher pH environment and result in a lower toxicity to normal tissues. The possible mechanism for an "On" compound to react with DNA is shown in FIG. 1.

For an "Off" compound, such as cis-[Pt(NH$_3$)(NH$_2$—CH$_2$CH$_3$—CO—O)]Cl, to become active, simple hydrolysis of the Pt—Cl bonds into Pt←OH$_2$ bond is not sufficient. It also needs to be in an environment with sufficient acidity so that the Pt—OCO bond can also be hydrolyzed into Pt←OH$_2$. The active form is uniquely differently from that of cisplatin. Characteristics of the active form are the same as described above for an "On" compound. The possible mechanism for an "Off" compound to react with DNA is shown in FIG. 2.

Neither cisplatin nor carboplatin is able to reversibly change into a non-active form.

Using a dynamic platinum compound, as disclosed in the present invention, under a cancerous environment with lower pH, significant amounts of said compounds are activated, thus, essential efficacy is maintained. Conversely, the dynamic compounds will result in lower toxicity under a normal biological environment (higher pH). Therefore, these platinum compounds disclosed herein appear to be unique and significantly better than traditional anticancer platinum compounds.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION

Figure 1:
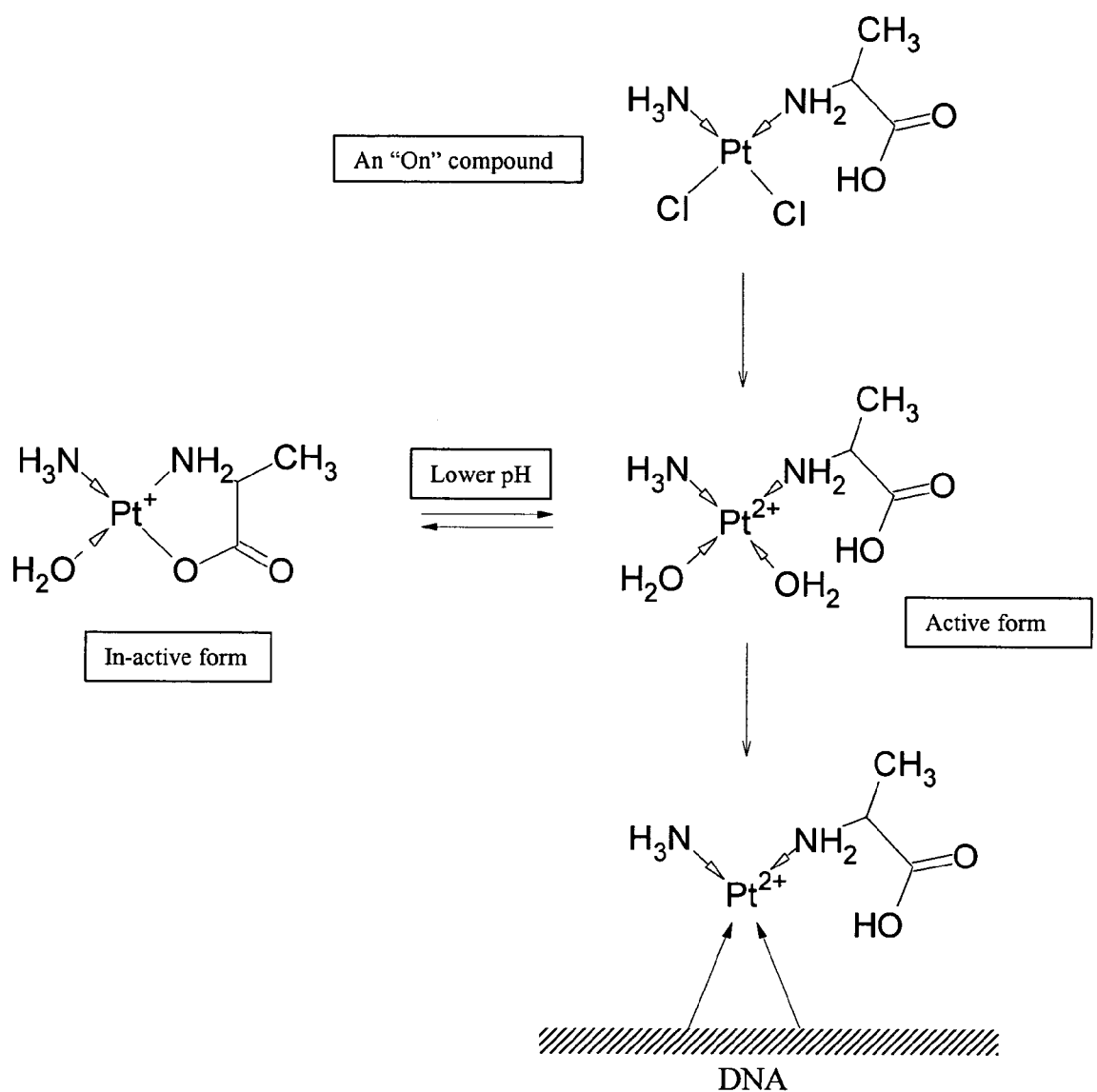
FIG. 1 shows a possible mechanism for an "On" compound, cis-[Pt(NH$_3$)(NH$_2$—CHCH$_3$—CO—OH)]Cl$_2$, to react with DNA.

Based on the objects, a plurality of On-and-Off platinum compounds are disclosed in the present invention. These platinum compounds can resolve the efficacy-toxicity dilemma because of their ability to become active and inactive reversibly.

The general structures of said dynamic platinum compounds in the present invention are shown as follow:

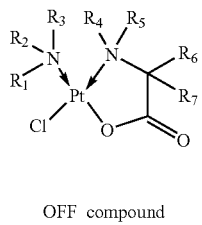 or 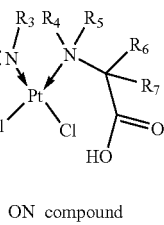

OFF compound      ON compound wherein each of $R_1$, $R_2$, $R_3$, $R_4$, $R_5$, $R_6$, and $R_7$, independently, is hydrogen, —OH, —CH$_2$—$_{OH}$, —$_{CH2}$—CH$_2$—OH, —CH$_2$—OH—CH$_3$, —CH$_2$—CH$_2$—CH$_2$—OH, —CH$_2$—CH(CH$_3$)OH, —O—CH$_3$, —O—CH$_2$—CH$_3$, —O—CH$_2$—CH$_2$—CH$_3$, —CH$_2$—C$_6$H$_6$, —CH$_2$—C$_6$H$_5$—OH, —CH$_2$—COOH, —CH$_2$—CH$_2$—COOH, lower alkyl, or $R_1$, $R_2$, $R_3$ together with the attached N is pyridine;

wherein "lower alkyl" means a linear, or branched hydrocarbon group containing from about 1 to 6 carbons, preferably from 1 to 3 carbons. Preferred lower alkyl groups include methyl, ethyl, and propyl.

To our best knowledge, none of the above Platinum compounds were published and none were disclosed as agents for cancer treatment.

Some examples of the dynamic compounds in the present invention are shown as follows

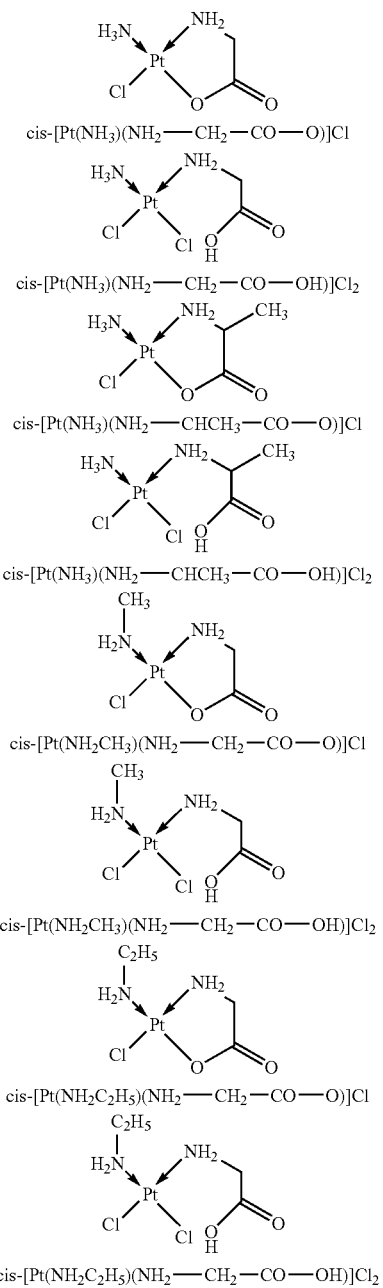

The following examples indicate the synthesis and the in vitro efficacy of cis-[Pt(NH$_3$)(NH$_2$—CH$_2$CH$_3$—CO—O)]Cl (code name: UTD4-A).

EXAMPLE 1

Synthesis of cis-[Pt(NH$_3$)(NH$_2$—CHCH$_3$—CO—O)]Cl (Code Name: UTD-4-A) (Formula: C$_3$H$_9$N$_2$O$_2$ClPt, mw 335.5)

Dissolve 360.3 mg of KPt(NH$_3$)Cl$_3$ and 90.3 mg of L-Alanine in ca. 35 mL DI water and mix well. Add a small amount of 0.1 N NaOH to facilitate the reaction and heat it for ca. 2 hours at below 75° C. Concentrate the aliquot to <10 mL and let it sit at room temperature to obtain the crystals. Filter and keep the light yellow crystals. Dry it at 60° C. for several hours. Elemental analysis results: theory (C=10.73%, H=2.68%, N=8.34%); found (C=10.84%, H=2.67%, N=8.39%)

EXAMPLE 2

Anti-cancer Effect of UTD-4-A in vitro

1. Test Substance and Dosing Pattern

UTD-4-A was dissolved in 100% DMSO and then diluted with sterile distilled water to obtain initial working solutions of 10000, 1000, 100, 10 and 1 mM in 40% DMSO. A 100-fold dilution was further made in culture media to generate final assay concentrations of 100, 10, 1, 0.1 and 0.01 mM in 0.4% DMSO.

2. Cell Culture Media

| Cell Lines | Culture Medium |
|---|---|
| HT-29 | McCoy's 5A medium, 90%; Fetal Bovine Serum, 10% |
| OVCAR-3 | RPMI 1640, 80%; Fetal Bovine Serum, 20%, supplemented with 0.01 mg bovine insulin per ml |

All media were supplemented with 1% Antibiotic-Antimycotic.

3. Cell Lines

| Cell Name | Source | Type of Cell Line |
|---|---|---|
| HT-29 | ATCC HTB-38 | Adenocarcinoma, colon, moderately well-differentiated grade II, human |
| OVCAR-3 | ATCC HTB-161 | Adenocarcinoma, ovary, human |

4. Evaluation of Anti-proliferative Activity

Aliquots of 100 ml of cell suspension (about 2.5×10³/well) were placed in 96-well microtiter plates in an atmosphere of 5% CO2 at 37° C. After 24 hours, 100 mL of growth medium and 2 ml of test solution or vehicle (40% DMSO) were added respectively per well in duplicate for an additional 72-hour incubation.

Thus, the final concentration of DMSO was 0.4%. The test compound, UTD-4-A, was evaluated at concentrations of 100, 10, 1, 0.1 and 0.01 mM. At the end of incubation, 20 ml of 90% alamarBlue reagent was added to each well for another 6-hour incubation before detection of cell viability by fluorescent intensity. Fluorescent intensity was measured using a Spectraflour Plus plate reader with excitation at 530 nm and emission at 590 nm.

5. Results

As shown in Table 1 and Table 2, UTD-4-A caused significant growth inhibition at concentrations between 10 and 100 μM relative to the vehicle-treated control in the 2 tumor cell lines.

TABLE 1

Effect of UTD-4-A on Colon, HT-29 Tumor Cells

| | Percent Growth (Mean of 2) | | |
|---|---|---|---|
| Vehicle | 100 μM | 10 μM | 1 μM |
| 100 | 41 ± 4 | 95 ± 8 | 100 ± 6 |

TABLE 2

Effect of Test Substances on Ovary, OVCAR-3 Tumor Cell

| | Percent Growth (Mean of 2) | | |
|---|---|---|---|
| Vehicle | 100 μM | 10 μM | 1 μM |
| 100 | 30 ± 3 | 85 ± 3 | 100 ± 6 |

The dynamic platinum compounds disclosed in the present invention are unique in that they have a unique mechanism to react with DNA, which is different from that of cisplatin or carboplatin. The unique design of the dynamic platinum compounds allow them to be less toxic to normal tissues while maintaining substantial efficacy. The difference can illustrated by FIGS. 1, 2, and 3 (Cisplatin and Carboplatin)

To our best knowledge, the dynamic platinum compounds and their use for treating cancer in the present invention were not previously disclosed in the public domain.

In a particular aspect, the present invention provides methods for the treatment of various malignancies. Treatment methods will involve treating an individual with an effective amount of the platinum compound disclosed in this invention, as described herein. An effective amount is described, generally, as that amount sufficient to detectably and repeatedly ameliorate, reduce, minimize or limit the extent of a disease or its symptoms. More rigorous definitions may apply, including elimination, eradication or cure of disease.

Cancer cells grow rapidly and require more energy than normal cells. As a result, some cancer cells switch from mitochondrial respiration to glycolysis; significant glycolysis results in enhanced production of lactic acid that reduces local pH. The microenvironment of a tumor can have a pH as low as 5.2 (Laurencot C. M. et. al., Oncol. Res, 7:371–379, 1995; Raghunand N. et. al., Biochem. Pharmacol., 57: 309–312, 1999.).

All platinum compounds disclosed in the present invention are dynamic; they can be hydrolyzed and then be transformed back and forth between the active form and non-active form. Thus, this dynamic system is also referred to as an On-and-Off system. Depending on how acidic a biological environment is, different amount of the dynamic platinum compound is converted from the non-active form to the active form. The more acidic the environment is, the more non-active form will be converted into active form.

It is clear that the active form will be effective in killing cancer cells and the non-active form will not have much cytotoxicity, thus, the side effects to the host tissues are significantly reduced.

Figure 2:
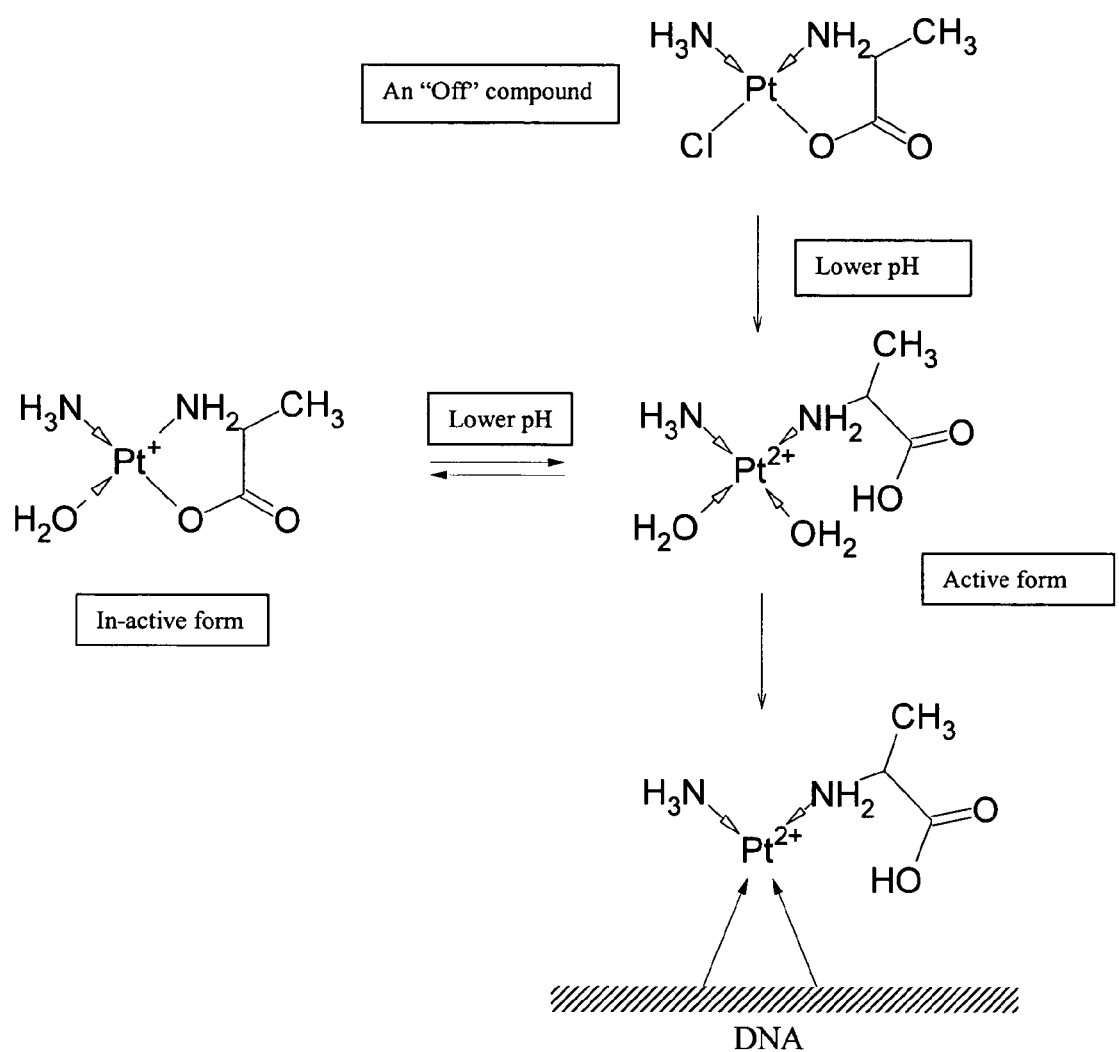
FIG. 2 shows a possible mechanism for an "Off" compound, such as cis-[Pt(NH$_3$)(NH$_2$—CHCH$_2$—CO—O)]Cl, to react with DNA.
Figure 3:
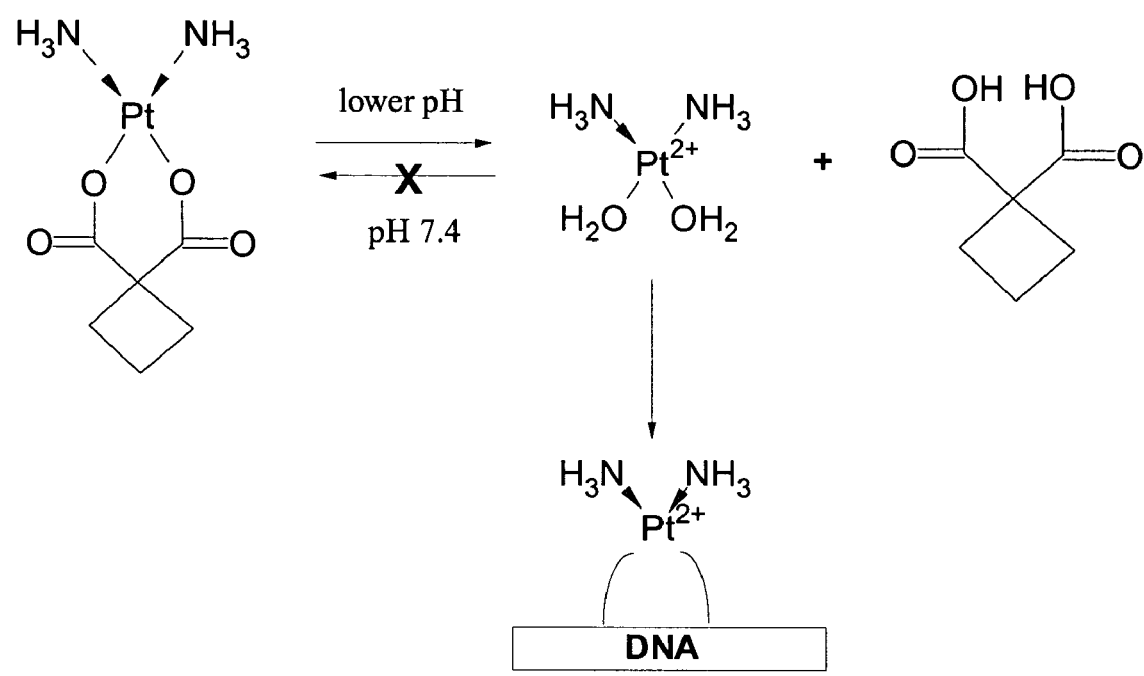
FIG. 3 shows a mechanism for carboplatin to react with DNA.

As the active form binds onto DNA to inhibit the replication of cancer cells, its concentration decreases. This decreased concentration of the active form pushes the non-active form into active form to reach a chemical equilibrium. The schematic explanation is shown in FIG. 1 and FIG. 2.

Therefore, the present invention discloses an improved method for treating cancer by administering the dynamic platinum compound disclosed herein.

Because a variety of ligands may be used to form a variety of On-and-Off platinum compounds, these platinum compounds can have significantly different physical properties (such as affinity, solubility, permeability, stereo effect, etc.) from those of cisplatin, carboplatin, or oxaliplatin. Therefore, it is conceivable that they would be useful in treating cancers that are not treated by cisplatin, carboplatin, or oxaliplatin. For example, oxaliplatin's ligand is different from that of cisplatin and carboplatin, and it was approved for treating colon cancer, which is not being treated by cisplatin or carboplatin.

The present invention discloses a method of treating cancer by said platinum compound wherein said cancer of the lung, brain, prostate, kidney, liver, ovary, endometrium, breast, skin, stomach, esophagus, head and neck, testicles, germ cancer, epithelial, colon, small intestine, thyroid, cervix, pancreas, glioblastoma, astrocytoma, oligodendroglioma, ependymomas, neurofibrosarcoma, meningia, lymphatic system and blood.

The present invention discloses a pharmaceutical composition comprising:
  i) a pharmaceutically acceptable dosage form of the platinum compound in claim 1, and
  ii) one or a plurality of pharmaceutically acceptable excipients.

The above pharmaceutically acceptable dosage form comprises between about 5 mg to about 1000 mg of the platinum compound. The therapeutic compositions of the present invention are advantageously administered in the form of injectable compositions either as liquid solutions or suspensions; solid forms suitable for solution in, or suspension in, liquid prior to injection may also be prepared. Additional formulations are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders. When the route is topical, the form may be a cream, ointment, salve or spray.

The present invention discloses a method comprising administering to a cancer patient a therapeutically effective amount of the above pharmaceutical composition; the pharmaceutically acceptable form is administered once every one to six weeks and the regimen may be repeated until remission of said cancer is observed.

In the above method, the administration is oral or parenteral. In addition, the method further comprises treating said cancer patient with a further cancer therapeutic agent. Said further cancer treating agent is a DNA damaging agent selected from the group consisting of verapamil, podophyllotoxin, procarbazine, mechlorethamine, cyclophosphamide, camptothecin, ifosfamide, melphalan, chlorambucil, bisulfan, nitrosurea, dactinomycin, daunorubicin, doxorubicin, bleomycin, plicomycin, mitomycin, etoposide (VP16), tamoxifen, taxol, transplatinum, 5-fluorouracil, vincristin, vinblastin and methotrexate.

Said further cancer treating agent also comprises radiation, which is selected from the group consisting of X-ray radiation, UV-radiation, γ-radiation, or microwave radiation.

The method of treating cancer disclosed in the present invention is effected by local delivery of said pharmaceutical composition, wherein said administering is effected by direct injection of a tumor in said cancer patient with said pharmaceutical composition.

The administration of said pharmaceutical composition may be effected endoscopically, intratracheally, intralesionally, percutaneously, intravenously, subcutaneously or intratumorally.

The method of treating cancer further comprises the step, prior to said administering, of resection of a tumor in said cancer patient.

These platinum compounds may also be used in the treatment of AIDS (Acquired Immune Deficiency Syndrome). Because of the potential ability of these complexes to hamper the DNA or RNA replication process, it is likely that these complexes are effective against the HIV (Human Immunodeficiency Virus) and may be used for the treatment of AIDS. Because the platinum(II) ion may be camouflaged by a variety of ligands, theses platinum(II) complexes are less likely to cause the self defense of the HIV. Thus, these platinum(II) complexes may be used to treat AIDS.

Therefore, it is also disclosed a method of treating Acquired Immune Deficiency Syndrome (AIDS) comprising administering orally or parenterally to an AIDS patient a therapeutically effective amount of a pharmaceutical composition comprising the platinum compound in the present invention.

According to the present invention, a series of such Pt compounds may be made employing a variety of ligands, which are derivatives of EDDA. Since EDDA is not expensive, the costs of its derivatives are expected to be reasonable. Therefore, the costs of platinum compounds made from these ligands should be reasonable, too.

Summary, Ramification, and Scope

In conclusion, a series of dynamic platinum compounds are disclosed in this invention. Also disclosed is a method of treating cancer comprising administering to a cancer patent said platinum compound.

Although the description above contains many specificities, these should not be construed as limiting the scope of the invention but as merely providing the illustrations of some of the presently preferred embodiments of this invention. Thus the scope of this invention should be determined by the appended claims and their legal equivalents, rather than by the examples given.

The invention claimed is:

1. A platinum compound comprising a structure:

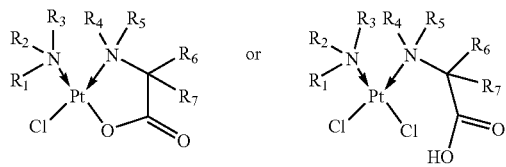

wherein each of $R_1$, $R_2$, $R_3$, $R_4$, $R_5$, $R_6$, and $R_7$, independently, is hydrogen, —OH, —CH$_2$—OH, —CH$_2$—CH$_2$—OH, —CH$_2$—OH—CH$_3$, —CH$_2$—CH$_2$—CH$_2$—OH, —CH$_2$—CH(CH$_3$)OH, —O—CH$_3$, —O—CH$_2$—CH$_3$, —O—CH$_2$—CH$_2$—CH$_3$, —CH$_2$—C$_6$H$_6$, —CH$_2$—C$_6$H$_5$—OH, —CH$_2$—COOH, —CH$_2$—CH$_2$—COOH, or lower alkyl, or $R_1$, $R_2$, $R_3$ together with the attached N is pyridine;

with a proviso that when each of $R_1$, $R_2$, $R_4$, $R_5$, and $R_7$ is hydrogen and $R_3$ is t-butyl, then $R_6$ is not hydrogen, methyl, —$CH_2$—$C_6H_6$, —$CH_2$—OH, i-butyl or i-propyl;

and with a further proviso that when each of $R_1$, $R_2$, $R_4$, $R_5$, $R_6$, and $R_7$ is hydrogen, then $R_3$ is not —$CH_2$—COOH.

2. The compound of claim 1, wherein the "lower alkyl" comprises a linear or branched hydrocarbon group comprising from 1 to 6 carbons.

3. The compound of claim 2, wherein the linear or branched hydrocarbon group comprises from 1 to 3 carbons.

4. The compound of claim 1, wherein the lower alkyl group is selected from the group consisting of methyl, ethyl, and propyl.

5. A method of treating cancer selected from the group consisting of cancer of the colon, ovaries, head and neck, brain, testicles, bladder, and combinations thereof, the method comprising administering to a cancer patient a therapeutically effective amount of the platinum compound of claim 1.

6. A pharmaceutical composition comprising:
  i) a pharmaceutically acceptable dosage form of the platinum compound of claim 1; and
  ii) one or a plurality of pharmaceutically acceptable excipients.

7. A method of treating cancer selected from the group consisting of cancer of the colon, ovaries, head and neck, brain, testicles, bladder, and combinations thereof, the method comprising administering to a cancer patient a therapeutically effective amount of the pharmaceutical composition of claim 6.

8. The method of claim 7, wherein said pharmaceutically acceptable dosage form comprises between about 5 mg and about 1000 mg of said platinum compound.

9. The method of claim 8, wherein said pharmaceutically acceptable form is administered once every one to four weeks.

10. The method of claim 9, wherein administration is repeated until remission of said cancer is observed.

11. The method of claim 7, wherein said pharmaceutical composition is administered orally.

12. The method of claim 7, wherein pharmaceutical composition is administered parenterally.

13. The method of claim 7, further comprising administering to said cancer patient a further chemotherapeutic agent selected from the group consisting of verapamil, podophyllotoxin, procarbazine, mechlorethamine, cyclophosphamide, camptothecin, ifosfamide, melphalan, chlorambucil, bisulfan, nitrosurea, dactinomycin, daunorubicin, doxorubicin, bleomycin, plicomycin, mitomycin, etoposide (VP16). tamoxifen, taxol, transplatinum, 5-fluorouracil, vincristin, vinblastin, methotrexate, and combinations thereof.

14. The method of claim 13, further comprising administering to said cancer patient a radiation selected from the group consisting of X-ray radiation, UV-radiation, γ-radiation, microwave radiation, and combinations thereof.

15. The method of claim 7, wherein said administering is effected by local delivery of said pharmaceutical composition.

16. The method of claim 7, wherein said administering is effected by direct injection of a tumor in said cancer patient with said pharmaceutical composition.

17. The method of claim 7, wherein said administering comprises delivering said pharmaceutical composition endoscopically, intratracheally, intralesionally, percutaneously, intravenously, subcutaneously, intratumorally or by combinations thereof.

18. The method of claim 7, further comprising resectioning a tumor in said cancer patient prior to said administering.

19. A method of treating AIDS comprising administering orally or parenterally to an AIDS patient a therapeutically effective amount of a pharmaceutical composition comprising the platinum compound of claim 1.

* * * * *